US007886576B2

(12) United States Patent
Uber (10) Patent No.: US 7,886,576 B2
(45) Date of Patent: Feb. 15, 2011

(54) PHOTOACOUSTIC GAS SENSOR (75) Inventor: Robert E. Uber, Pittsburgh, PA (US)

(73) Assignee: Mine Safety Appliances Company, Pittsburgh, PA (US)

( * ) Notice: Subject to any disclaimer, the term of this patent is extended or adjusted under 35 U.S.C. 154(b) by 724 days.

(21) Appl. No.: 11/897,754

(22) Filed: Aug. 31, 2007

(65) Prior Publication Data
US 2008/0252891 A1 Oct. 16, 2008

Related U.S. Application Data (60) Provisional application No. 60/857,042, filed on Nov. 6, 2006.

(51) Int. Cl.
G01N 21/61 (2006.01)
G01N 29/02 (2006.01)
(52) U.S. Cl. .................. 73/24.02; 356/432; 356/437
(58) Field of Classification Search .............. 73/24.02; 356/432, 433, 437
See application file for complete search history.

(56) References Cited

U.S. PATENT DOCUMENTS

| 4,818,882 | A | 4/1989 | Nexo et al. ............ 250/343 |
| 6,006,585 | A | 12/1999 | Forster .................. 73/24.01 |
| 7,034,943 | B1 | 4/2006 | Moeckli et al. .......... 356/423 |
| 2003/0112019 | A1 | 6/2003 | Forster et al. ............ 324/633 |

FOREIGN PATENT DOCUMENTS

EP 1574840 A1 * 9/2005

OTHER PUBLICATIONS

Long, Edward M. ,Sennheiser HDC451 Noise-Cancelling Earphones, Audio, Dec. 1995, pp. 52-56.

* cited by examiner

*Primary Examiner*—Lisa M Caputo
*Assistant Examiner*—Punam Roy
(74) *Attorney, Agent, or Firm*—Hank E. Bartony, Jr.; James G. Uber (57) ABSTRACT

A photoacoustic sensor includes a sensor system for photoacoustic detection, at least one noise canceling pressure sensor and a control system in operative connection with the noise canceling pressure sensor to actively cancel the effects of noise in the environment on the sensor system. Another photoacoustic sensor includes a measurement volume, a source of light energy, a photoacoustic pressure sensor, and at least one vibration canceling sensor (for example, a microphone or an accelerometer). A further photoacoustic sensor includes a measurement volume, a source of light energy and a photoacoustic pressure sensor. The measurement volume has an inner surface that is continuously curved over substantially the entire inner surface other than where a window in optical connection with the source of light intersects the measurement volume.

20 Claims, 5 Drawing Sheets

PHOTOACOUSTIC GAS SENSOR

RELATED APPLICATIONS

This application claims priority on U.S. Provisional Patent Application No. 60/857,046 filed Nov. 6, 2006, the entire disclosure of which is incorporated herein by reference

BACKGROUND OF THE INVENTION

The present invention relates generally to gas sensors, and, particularly, to photoacoustic gas sensors.

The following information is provided to assist the reader to understand the invention disclosed below and the environment in which it will typically be used. The terms used herein are not intended to be limited to any particular narrow interpretation unless clearly stated otherwise in this document. References set forth herein may facilitate understanding of the present invention or the background of the present invention. The disclosure of all references cited herein are incorporated by reference.

The use of diffusive gas sensors to detect the concentration level of gaseous species of interest using the photoacoustic effect is well known. For example, U.S. Pat. No. 4,740,086 discloses the use of a diffusive photoacoustic gas sensor to convert the optical energy of an amplitude modulated light source into acoustic energy when the light mechanically and thermally excites the gaseous species of interest as it diffuses into a sensing chamber upon which the light is incident. Sound waves of an intensity corresponding to the concentration level of the gas within the chamber are generated as the light radiation absorbed by the gas creates pressure fluctuations of a magnitude proportional to the number of gas molecules located within the sensing chamber. These sound/pressure waves are detected by an acoustic detector such as a microphone.

Photoacoustic gas sensors can have mechanical valves to let in the sample gas when open, which then close to trap the sample gas and block external acoustical noise. Valves have the disadvantages of requiring energy to operate and having moving parts which wear leading to limited lifetimes (typical 0.5 to 3 years). A gas diffusion element such as described in U.S. Pat. No. 4,740,086, could be used to simultaneously allow gas diffusion and attenuate external acoustical noise. But the degree of attenuation and the rate of gas diffusion is a compromise. A faster gas diffusion rate typically accompanies reduced external noise attenuation. Thus a photoacoustic sensor that uses a diffusion element (as opposed to valves) is more susceptible to external acoustical noise from the environment entering through the diffusion element.

The output signal of a diffusive photoacoustic sensor is susceptible to noise created by interference from outside sources of air pressure fluctuations, such as wind, vibration and acoustic phenomena. To eliminate such noise, one may incorporate some means of attenuating extraneously generated pressure waves, while attempting to allow the gas to freely diffuse into the sensing chamber for detection. For example, porous members through which gas relatively readily diffuses, but which attenuate the effect of external pressure fluctuations, are often placed at the entrance of photoacoustic sensors. However, one must balance this attenuating effect with a corresponding increase in response time. In that regard, introduction of a sound/pressure attenuating element or elements to reduce noise typically results in a corresponding loss of responsiveness to changing analyte concentration. The specifications for combustible gas detectors of the Instrument Society of America (ISA) require gas concentration level measurement stability at wind speeds of up to 5 meters per second (m/s) with a corresponding response time (to 60% of full scale indication) of less than 12 seconds.

U.S. Pat. No. 7,034,943 discloses a sound/pressure damping element (SDE) designed for use in a diffusive, non-resonant photoacoustic gas sensor (detector). The SDE reduces external, low-frequency noise to acceptable levels while permitting the photoacoustic detector (sensor) to maintain an adequate response time to changing gas concentration levels. In general, the photoacoustic detector of U.S. Pat. No. 7,043,943 includes a first volume having a sensor system for photoacoustic detection therein. The first volume is in fluid connection with the environment through an opening so that the gas analyte can diffuse into the first volume through the opening. The photoacoustic detector of U.S. Pat. No. 7,043,943 further includes a second volume (an SDE volume) in connection with the first volume such that pressure readily equalizes between the first volume and the second volume and such that diffusion of analyte gas from the first volume to the second volume is hindered (or slowed as compared to diffusion of analyte gas into the first volume from the environment). Typically, the second volume is substantially larger (for example, 300 mL) than the first volume (for example, 1 mL) to enhance attenuation of external pressure fluctuations. The first volume can, for example, be connected to the second volume by a channel that is shaped to limit diffusion of analyte gas therethrough. The channel may, for example, be elongated and of small cross section compared to the opening into the first volume. Disadvantages of an SDE include the large gas volume required (especially for explosive gases), the time for the sample gas to fill the large SDE, and the physical size/bulk of the SDE.

U.S. Pat. No. 7,106,445 discloses a photoacoustic gas sensor utilizing diffusion having a sensing volume and an acoustic pressure sensor volume containing an acoustic pressure sensor such that the fluid connection between the sensing volume and the acoustic pressure sensor volume restricts the flow of analyte gas therethrough but does not restrict the transmission of the photoacoustic signal therethrough. The methods and devices of U.S. Pat. No. 7,106,445 provide for controlling the diffusion of the analyte gas within a diffusive photoacoustic gas sensor to improve the response time of the sensor as, for example, compared to a sensor with a large SDE.

U.S. Pat. No. 6,006,585 discloses a photoacoustic (or optoacoustic) gas sensor including a sensor body, a light source, a measurement cell with a gas-permeable membrane, a measurement microphone, and an optical measurement filter between the light source and the measurement cell. The sensor also includes a reference cell that is separate from the measurement cell. The reference cell is generally identical in volume and form to the measurement cell. The reference cell and the measurement cell each include a gas inlet. The reference cell has a reference microphone that is shielded against photoacoustic signals from the gas to be detected. In that regard, the reference cell is substantially free from intensity-modulated optical radiation having an absorption wavelength of the gas to be detected. The measurement signal, which indicates gas concentration, is obtained by subtraction of the signals from the measurement and reference microphones. As a result of the subtraction, interference signals caused by vibrations or air pressure fluctuation are purportedly eliminated (the former through use of the reference microphone which receives no photoacoustic signals from the gas to be measured, and the latter by virtue of the spatially separate reference cell with the reference microphone). See col. 1, line 49 to col. 2, line 7.

As discussed briefly above, photoacoustic sensors can also be sensitive to vibrational energy in their environment of operation. U.S. Pat. No. 4,818,882, for example, discloses the use of two opposing microphones for reducing sensitivity to vibration. The microphones are turned oppositely and are symmetrically positioned about the center of gravity of the air contained in the measuring chamber. The signals of the two opposing microphones are summed to reduce the effect of vibration on the sensor output. Uniform microphones are required for simultaneous compensation of the vibration signal from both the air and the membrane.

Although advances have been made in the field of photoacoustic sensors, it remains desirable to develop improved photoacoustic gas sensors, devices for use in photoacoustic gas sensors and methods of fabricating photoacoustic gas sensors.

SUMMARY OF THE INVENTION

Generally, the present invention provides a photoacoustic sensor for measuring an analyte gas in an environment. In one aspect, the photoacoustic sensor includes a sensor system for photoacoustic detection, at least one noise canceling pressure sensor and a control system in operative connection with the noise canceling pressure sensor to actively cancel the effects of noise in the environment on the sensor system. The sensor system typically includes a measurement volume, a source of light energy and a photoacoustic pressure sensor.

In several preferred embodiments, the noise canceling pressure sensor is a first microphone and the photoacoustic pressure sensor is a second microphone. The noise canceling pressure sensor (for example, a microphone) can be in acoustic connection with an initial volume, which is in connection with the measurement volume. The photoacoustic sensor can further include a barrier between the measurement volume and the initial volume. The barrier can include a valve. The barrier between the measurement volume and the initial volume can alternatively include a first diffusion element operative to attenuate pressure waves while allowing diffusion of analyte gas molecules therethrough. The photoacoustic sensor can further include a second diffusion element positioned between the initial volume and an inlet of the photoacoustic gas sensor. The second diffusion element is operative to attenuate pressure waves while allowing diffusion of analyte gas molecules therethrough. The first diffusion element and the second diffusion element can, for example, be sintered metal elements.

The photoacoustic sensor can further include a speaker which is operative to be driven with a signal generally inverse to an output signal of the noise canceling pressure sensor. In several embodiments, the speaker is driven only over a frequency range in the vicinity of the operational frequency of the photoacoustic sensor.

The volume of the initial volume can, for example, be no greater than ten times the measurement volume. The volume of the initial volume can also be no greater than five times the measurement volume. In several embodiments, the volume of the initial volume is no greater than the measurement volume.

The photoacoustic sensor can further include at least one vibration canceling sensor (for example, a microphone or an accelerometer) that is not in acoustic connection with the measurement volume or with the environment. The photoacoustic microphone and the vibration canceling sensor can, for example, be mounted upon a common surface.

In another aspect, the present invention provides a photoacoustic sensor including a measurement volume, a source of light energy, a photoacoustic microphone, and at least one vibration canceling sensor (for example, a microphone or an accelerometer). The vibration canceling sensor is not in acoustic connection with the measurement volume or with the environment. In several embodiments, the photoacoustic sensor is a first microphone, and the noise canceling sensor is a second microphone. The photoacoustic microphone and the vibration canceling microphone can, for example, be positioned to be in generally the same plane or in generally parallel planes. The photoacoustic microphone and the vibration canceling microphone can, for example, be mounted upon a common surface.

The photoacoustic sensor can further include at least one noise canceling pressure sensor and a control system in operative connection with the noise canceling pressure sensor to actively cancel the effects of noise in the environment on the sensor system. The noise canceling pressure sensor can be a microphone. As described above, the photoacoustic sensor can further include a speaker which is operative to be driven with a signal generally inverse to an output signal of the noise canceling pressure sensor.

In a further aspect, the photoacoustic sensor includes a measurement volume, a source of light energy and a photoacoustic pressure sensor. The measurement volume preferably has an inner surface that is continuously curved over substantially the entire inner surface other than where a window in optical connection with the source of light intersects the measurement volume. In that regard, in several embodiments the inner surface of the measurement volume (excluding, that where the window intersects the measurement volume) is curved over at least 90% thereof, or even over at least 95% thereof. If the surface of the source of light is also curved, the measurement volume (which is defined, in part, by its intersection with the source of light) can be continuously curved over substantially the entire inner surface thereof. In several embodiments, the inner surface is generally spherical over substantially the entire inner surface other than where the window intersects the measurement volume.

The present invention, along with the attributes and attendant advantages thereof, will best be appreciated and understood in view of the following detailed description taken in conjunction with the accompanying drawings.

DETAILED DESCRIPTION OF THE INVENTION

Figure 1A:
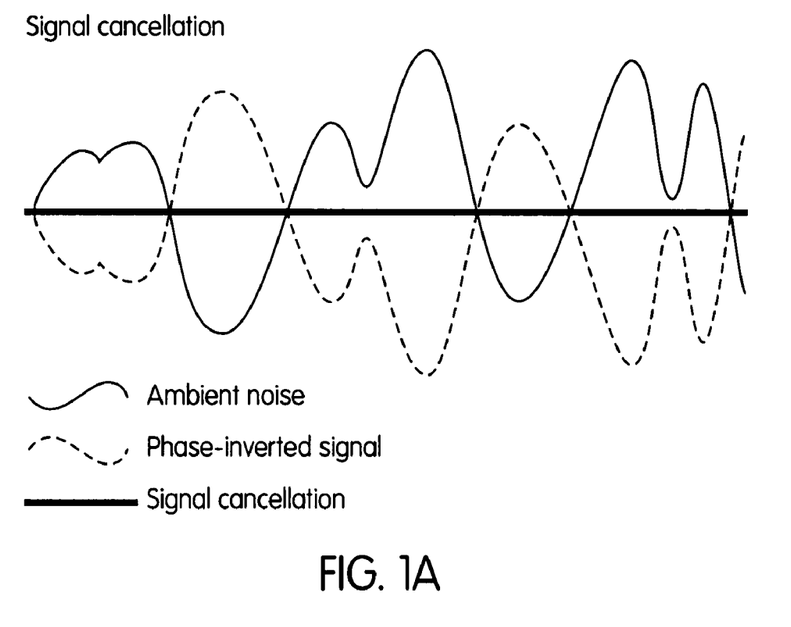
FIG. 1A illustrates a graphic representation of signal cancellation wherein ambient noise is canceled using a phase-inverted signal.
Figure 1B:
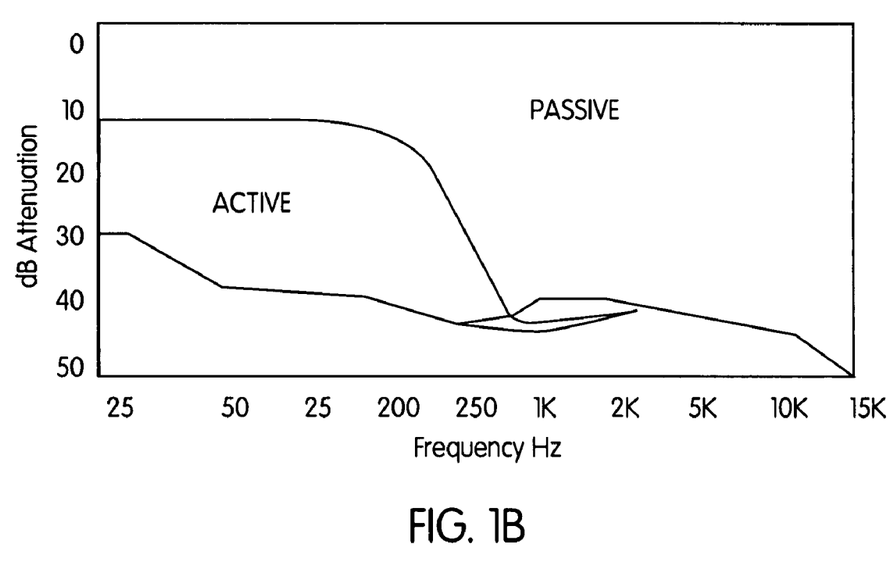
FIG. 1B illustrates a graphic representation of active and passive noise reduction.

In general, active noise compensation can operate on the principle of phase inversion, wherein sound waves are cancelled out by a 180° phase inversion of the sound waves as illustrated in FIG. 1A. See, for example, Aviation Headsets with NoiseGard™ Active Noise Compensation—Introduction, Sennheiser Publ. May 2002. Noise cancellation can, for example, be effected using an electret microphone capsule and feedback circuitry. Electronic circuitry can be used to process ambient noise, phase inverting it by 180° and mixing this phase-inverted noise with the original ambient noise. Unwanted noise is thus significantly reduced. FIG. 1B illustrates that noise cancellation can reduce low frequency noise by one or two decades in the NoiseGard™ headsets available from Sennheiser.

The present inventor has discovered that active noise compensation/cancellation methods and devices can be utilized in connection with photoacoustic sensors with surprisingly good results. As used herein the terms "active cancellation" or "active noise cancellation" refer to a process of measuring a level of noise and generating a signal to cancel, compensate for, or reduce the effects of the noise. As used herein, the term "cancel" and related terms (for example, "canceling" or "cancellation") refer to any reduction of an effect, including complete elimination thereof. The signal can be used to drive a speaker to acoustically cancel the noise. Alternatively, the signal can be used to effect analog or digital signal processing to cancel or compensate for the noise. In general, in the present invention, it is desirable to actively cancel or compensate for noise/pressure waves in the frequency range of operation of the photoacoustic sensors of the present invention.

Figure 2:
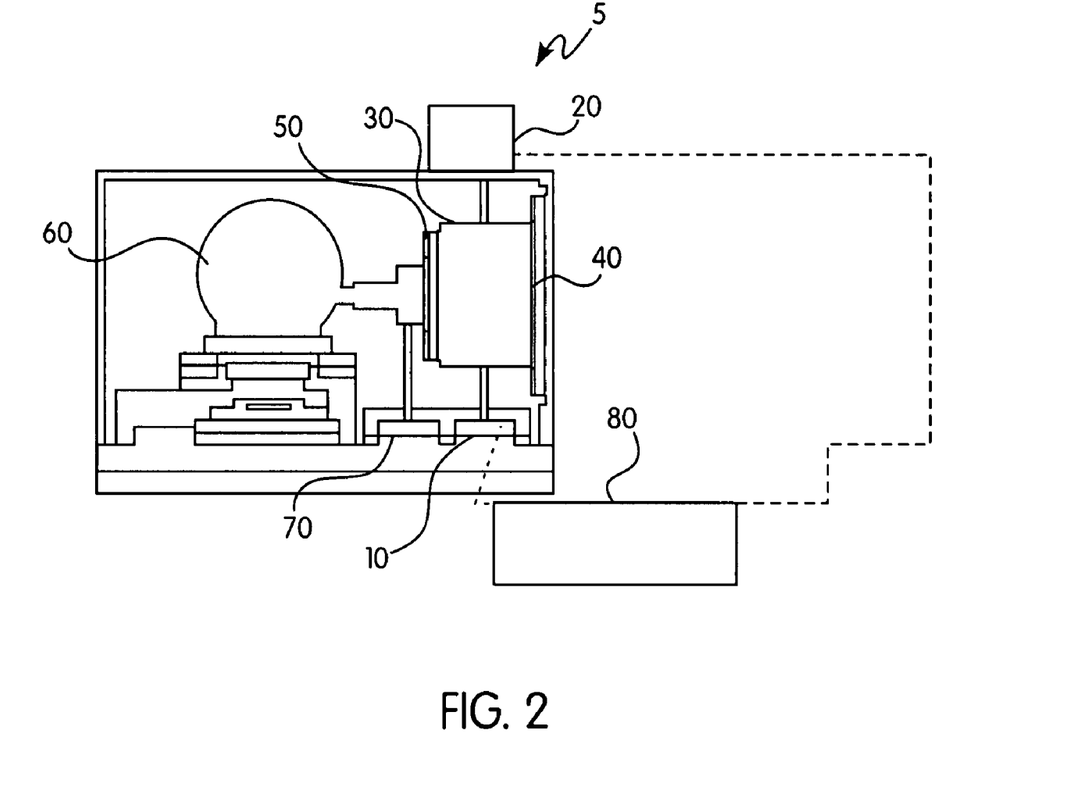
FIG. 2 illustrates a cross-sectional view of an embodiment of a photoacoustic gas sensor of the present invention including an initial volume having (in acoustic connection therewith) a speaker and a noise canceling microphone adapted to actively cancel noise.

FIG. 2 illustrates an embodiment of a photoacoustic sensor 5 of the present invention in which a relatively small volume (typically less than approximately 1 ml) with active noise cancellation replaces the relatively large SDE volume (approximately 350 ml) in a photoacoustic sensor similar to that disclosed in U.S. Pat. No. 7,034,943. Sensors as disclosed in U.S. Pat. No. 7,034,943 are, for example, commercially available from Mine Safety Appliances Company under the trademark CHILGARD® LS. In photoacoustic sensor 5 of FIG. 2, a microphone 10 (or other pressure sensing device, such as a piezoelectric pressure transducer) and a small speaker 20 are placed in communicative connection with an initial volume 30 between a first or outer diffusion element 40 and a second or inner diffusion element 50.

In the embodiment of FIG. 2, diffusion elements 40 and 50 can, for example, be a porous material such as a metal sinter disk. Diffusion elements suitable for use in the present invention permit the diffusion of molecules of the gas species of interest (that is, the analyte gas or gases) through initial volume 30 and into a sensing (or measurement) volume or chamber 60 of photoacoustic detector 5, while attenuating noise/pressure waves. As known in the art, sinter disk 40 acts to attenuate external sources of pressure waves by impeding the progress of air pressure waves incident upon the photoacoustic cell gas inlet, while offering only minimal resistance to the diffusion of gas molecules into photoacoustic sensor 5 from the inlet. In the illustrated embodiment of FIG. 2, second or inner sinter disk 50 also acts to attenuate external sources of pressure waves by further impeding the progress of any air pressure waves that pass through the first sinter disk 40. Like sinter disk 40, sinter disk 50 preferably offers only minimal resistance to the diffusion of gas molecules into photoacoustic cell measurement chamber 60.

As in photoacoustic sensors in general, sound waves of an intensity corresponding to the concentration level of the analyte gas are generated when optical energy from light incident upon sensing chamber 60 is converted into acoustic energy upon absorption by the analyte gas, causing mechanical excitation of the analyte gas molecules to generate air pressure fluctuations of an intensity proportional to the number of gas molecules located within sensing chamber 60. The sound/pressure waves in the sensing chamber 60 are detected by microphone 70 or other pressure sensing device (for example, a piezoelectric transducer).

Speaker 20 is driven with the inverse signal of microphone 10 (see FIG. 1A). An active noise cancellation feedback loop can, for example, be constructed from either analog circuit components or digital circuit components in processing/control circuitry 80. Speaker 20 can, for example, be driven only near or in the vicinity of the photoacoustic frequency range of operation. Operating over such a reduced frequency range reduces power consumption, reduces the risk of saturating speaker 20, and can increase the stability of the active noise cancellation feedback loop. Speaker 20 can, for example, be driven in a range 25% (or even 10%) above and below the operational frequency range of the photoacoustic sensor (on a logarithmic scale). In several embodiments, the operational frequency of the photoacoustic sensors of the present invention is less than 20 Hz (for example, in the range of approximately 8 to 16 Hz.). A roll-off of, for example, approximately 3 dB per decade in cancellation of noise around or in the vicinity of the operation frequency range can be suitable.

The volume of initial volume 30 can, for example, be no greater than ten times the volume of sensing or measurement chamber 60, or be no greater than five times the volume of the sensing or measurement chamber 60. In several embodiments of the present invention, the volume of initial volume 30 was no greater than the volume of sensing or measurement chamber 60. For example, in several embodiments, the volume of sensing or measurement chamber 60 was approximately 1 ml, while the volume of initial volume 30 was approximately 0.5 ml.

Figure 3:
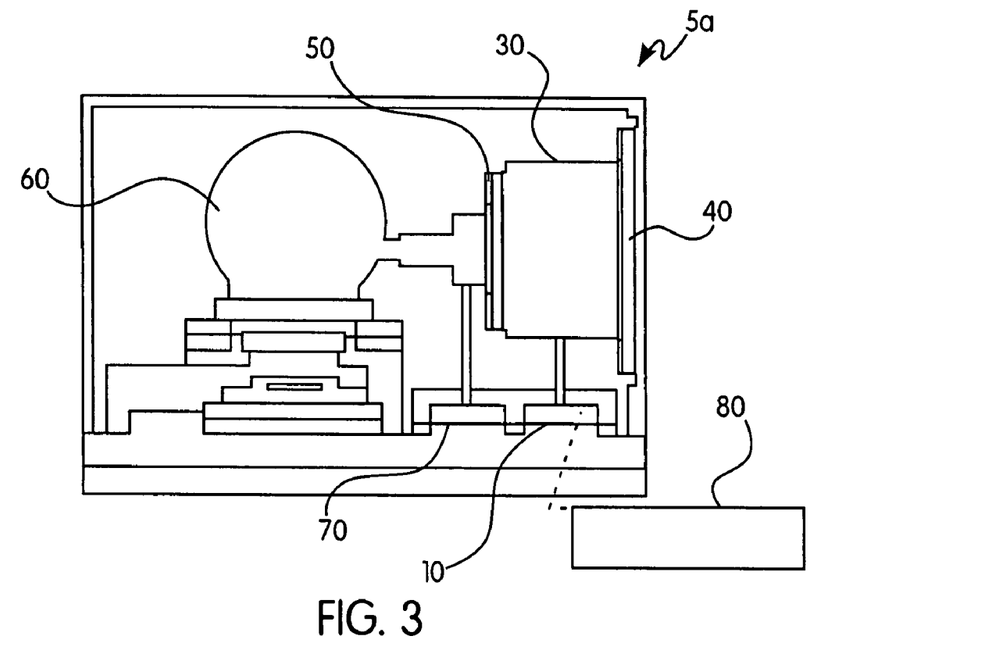
FIG. 3 illustrates a cross-sectional view of another embodiment of a photoacoustic gas sensor of the present invention including an initial volume having (in acoustic connection therewith) a noise canceling microphone adapted to actively cancel noise without a speaker.

In another or alternative embodiment of a photoacoustic sensor 5a of the present invention as illustrated in FIG. 3, the speaker is omitted. In this embodiment, noise canceling microphone 10 is used to measure external acoustical noise (pressure waves passing through sinter disk 40). The measured signal can be used in processing the photoacoustic signal. For example, the measured signal can be scaled and subtracted from the photoacoustic signal in either an analog or a digital form. The scaling of noise canceling microphone 10 is preferably limited to not saturate its output signal.

Figure 4:
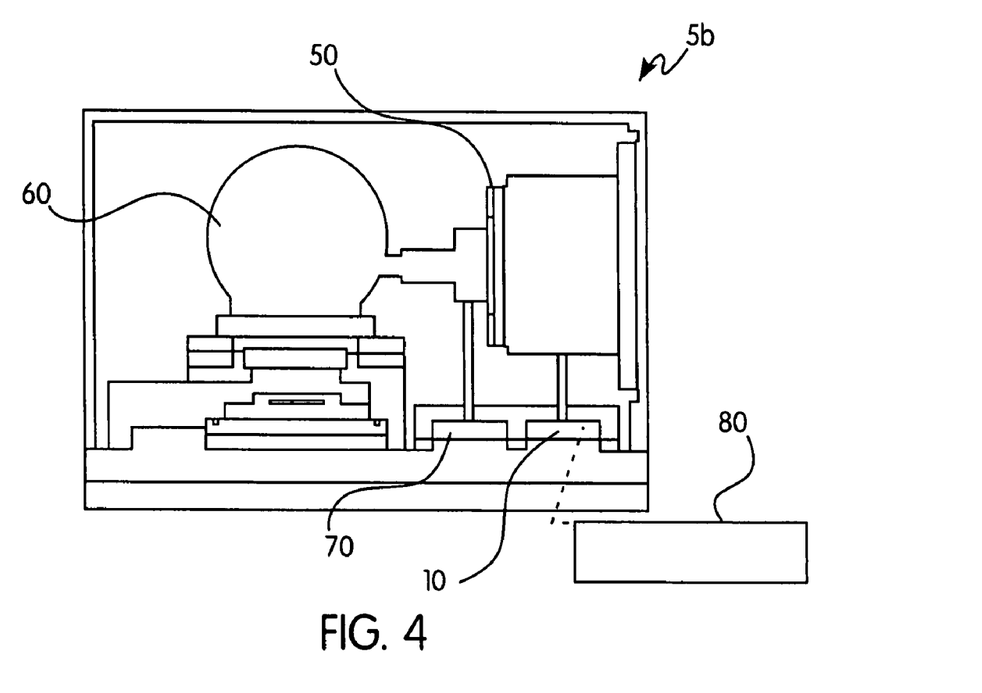
FIG. 4 illustrates a cross-sectional view of another embodiment of a photoacoustic gas sensor of the present invention including a noise canceling microphone adapted to actively cancel noise without a diffusion element adjacent the inlet of the photoacoustic gas sensor.

In another or alternative embodiment of a photoacoustic sensor 5b of the present invention as illustrated in FIG. 4, the outermost diffusion element or sinter disk can be omitted, essentially eliminating initial volume 30. Again, the scaling of noise canceling microphone 10 is preferably limited in this embodiment to not saturate its output.

Using signal processing techniques (as described, for example, in connection with FIGS. 3 and 4) can provide a number of benefits as compared to use of a speaker to acoustically cancel noise as described in connection with FIG. 2. For example, as compared to use of a speaker to acoustically cancel noise, use of signal processing can provide benefits including, but not limited to, reducing manufacturing cost, reducing operating power requirements, better accounting for phase lag, changing less in response/output over time (or improving stability) and decreasing the overall size of the photoacoustic sensor. However, use of a speaker to acoustically cancel noise can provide for noise reduction of greater amplitudes of noise than can be cancelled via signal processing. as the measurement microphone can more readily become saturated in the case of a signal processing system.

Figure 5:
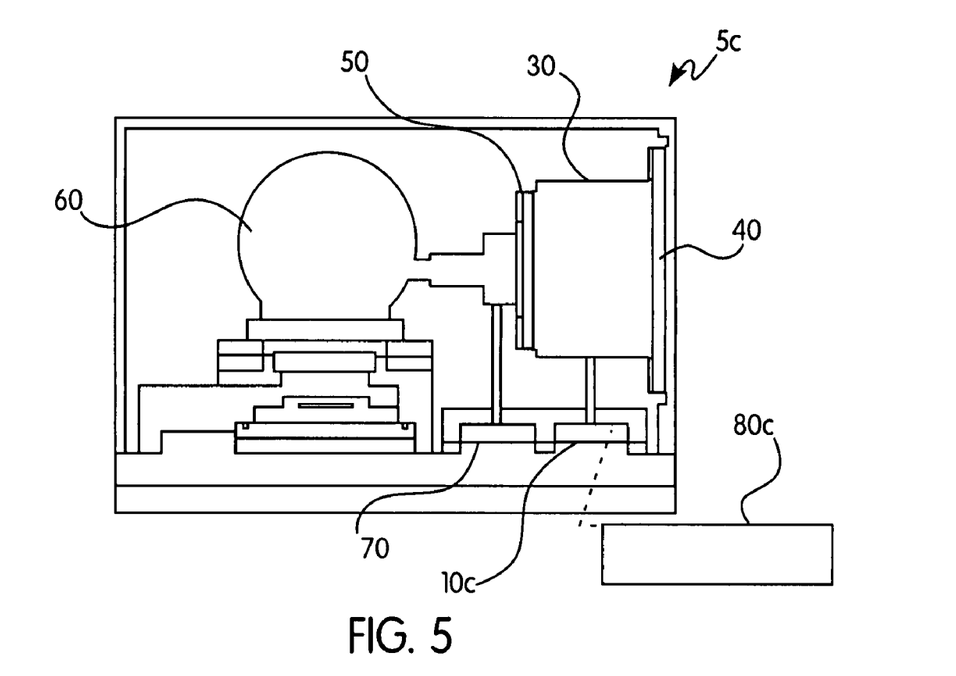
FIG. 5 illustrates a cross-sectional view of another embodiment of a photoacoustic gas sensor of the present invention including a vibration canceling microphone.

A photoacoustic sensor can also be susceptible to vibration and shaking. For example, photoacoustic sensors for detection of refrigerant gas can be mounted on or near supports for refrigeration compressors and are often subjected to substantial vibration. A vibration canceling sensor 10c (for example, a microphone or an accelerometer), as illustrated in FIG. 5 can be installed in the photoacoustic sensors of the present invention. In one embodiment, a microphone 10c was used. Microphone 10c can, for example, be installed in generally the same plane or in a generally parallel plane as photoacoustic microphone 70. However, microphone 10c is preferably not in optical or acoustical connection with sensing or measuring chamber 60, and not in acoustical connection with the surrounding environment as illustrated in FIG. 5. Because vibration cancellation microphone 10c is isolated from pressure fluctuations associated with acoustical connection with measuring chamber 60 and with the surrounding or ambient environment, it does not respond to acoustics, but responds to vibration only. There is no need, however, to isolate vibration canceling microphone 10c (or other vibration canceling sensor) from pressure changes to which vibration canceling microphone 10c is not sensitive (for example, barometric pressure changes). Microphone 10c and other components (including photoacoustic microphone 70) are preferably out of optical connection with measuring chamber 60 (such that infrared light does not impinge thereon) as elements or materials of microphone 10c and other components can sometimes interact with the infrared light to cause extraneous signals.

The signal from vibration canceling microphone 10c can, for example, be used in one or more algorithms to cancel or reduce vibrational effects from the photoacoustic signal in either analog or digital form. The signal from vibration canceling microphone 10c can, for example, be scaled and subtracted from the photoacoustic signal in the case that vibration canceling microphone 10c is positioned in the same orientation as photoacoustic microphone 70.

Figure 6:
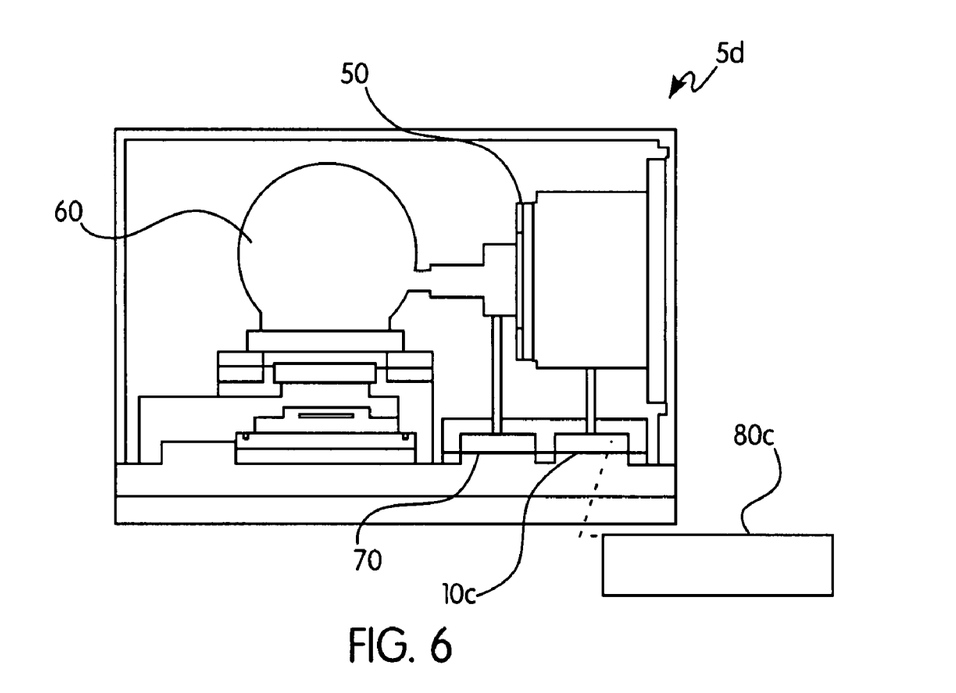
FIG. 6 illustrates a cross-sectional view of another embodiment of a photoacoustic gas sensor of the present invention including a vibration canceling microphone without a diffusion element adjacent the inlet of the photoacoustic gas sensor.

In general, installation of microphone 10c in generally the same plane or in a generally parallel plane as photoacoustic microphone 70 can simplify manufacturing as compared to, for example, use of opposing microphones (for example, within a measuring volume of a photoacoustic sensor). For example, microphone 10c and photoacoustic microphone 70 can be surface mounted in the same plane (for example, to a common surface such as to a printed circuit board or PCB) as illustrated in FIGS. 5 and 6. Further, installing microphone 10c outside of sensing or measurement chamber 60 and out of optical and acoustical connection with chamber 60 further simplifies manufacture.

In another or alternative embodiment of a photoacoustic sensor 5d of the present invention as illustrated in FIG. 6, the outermost diffusion element or sinter disk is omitted, essentially eliminating initial volume 30.

Omission of the outermost diffusion element (as illustrated in connection with FIGS. 4 and 6) can, for example, decrease response time of the photoacoustic sensors of the present invention. A barrier, such as innermost diffusion element 50 preferably remains between photoacoustic sensing or measuring chamber 60 and the ambient environment. Diffusion element 50 also separates (both optically and acoustically) the photoacoustic sensing or measuring chamber 60 from any noise canceling sensor.

As described above, relatively small initial volumes or no initial volume can be used in the noise canceling systems of the present invention, thereby eliminating the need for large SDE volumes or carefully matched reference volumes as used in a number of currently available photoacoustic sensors. A single gas inlet can be used in the photoacoustic sensors of the present invention. The microphone (and speaker in some embodiments) of the noise canceling, compensating or reducing systems of the present invention are placed in acoustical connection with the inlet upstream of the sensing or measuring chamber.

Figure 7:
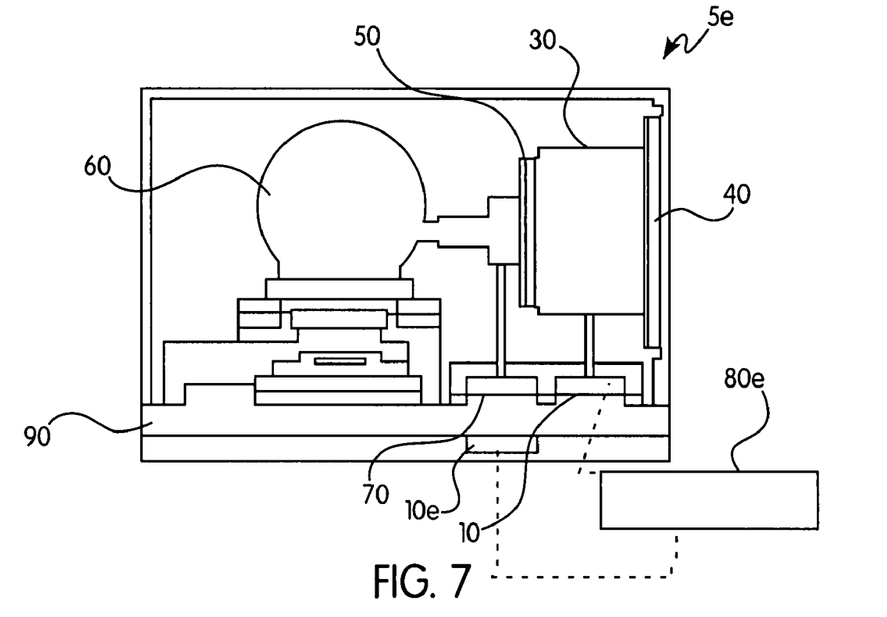
FIG. 7 illustrates a cross-sectional view of another embodiment of a photoacoustic gas sensor of the present invention including a noise canceling microphone and a vibration canceling microphone wherein the vibration canceling microphone is oriented opposite of the photoacoustic microphone.

FIG. 7 illustrates a photoacoustic sensor 5e of the present invention including both a sound canceling microphone 10 and a vibration canceling microphone 10e. In the embodiment of FIG. 7, vibration canceling microphone 10e is positioned in a plane generally parallel to the plane of photoacoustic microphone 70 but is oriented in an opposing direction. Vibration canceling microphone 10e can, for example, be surface mounted on an opposite side of printed circuit board 90. In the case that vibration canceling microphone 10e is oriented opposite to photoacoustic microphone 70, the cancellation algorithm is inverted as compared to the case when vibration canceling microphone 10e is in the same orientation as photoacoustic microphone 70. The signal from vibration canceling microphone 10e can, for example, be scaled and added to the photoacoustic signal.

Figure 8:
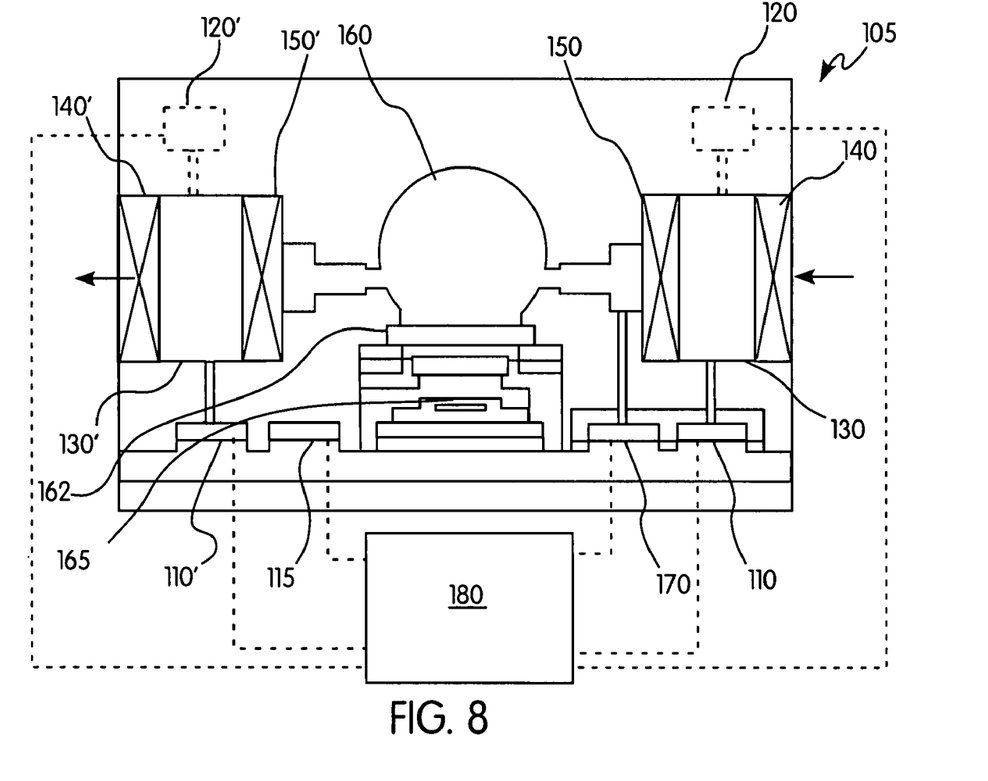
FIG. 8 illustrates a photoacoustic sensor of the present invention including a valve system, a noise canceling system of the present invention and a vibration canceling system of the present invention.

Although the use of one or more diffusion elements such as sinter disks is illustrated in the representative embodiments of FIGS. 2 through 7, one skilled in the art appreciates that the active noise and vibration cancellation or compensation systems, devices and methods of the present invention can also be used in connection with photoacoustic sensors including valve systems. FIG. 8, for example, illustrates a photoacoustic sensor 105 including valves 140, 140', 150 and 150', which are opened and closed in a synchronized manner as known in the photoacoustic sensors arts, to control passage of analyte gas into and out of photoacoustic gas sensor 105.

In the illustrated embodiment, first valve 140 is placed at an inlet of a first or initial volume 130. Volume 130 is separated from a second or measurement volume 160 by a second valve 150. Gas exits sensor 105 via a third volume 130' bounded by valves 150' and 140'. In a preferred embodiment, each of first volume 130 and third volume 130' includes a noise cancellation system in operative connection therewith. In that regard, a first noise canceling microphone 110 as described above is in acoustical connection with first volume 130. A noise canceling speaker 120 as described above can also be placed in acoustical connection with first volume 130. Similarly, a second noise canceling microphone 110' is in acoustical connection with third volume 130', and a second noise canceling speaker 120' can also be placed in acoustic connection with third volume 130'. Photoacoustic sensor 105 can further include vibration canceling sensor 115 (for example, a microphone or an accelerometer) as described above, which is isolated from photoacoustic connection with measurement volume 160 and isolated from acoustical connection with first volume, third volume and the surrounding environment. Each of microphones 110, 110' 170, and 115, as well as speakers 120 and 120' (if present) are in communicative connection with control system or circuitry 180.

Typically, extraneous noise or pressure waves are not as significant a problem in photoacoustic sensors equipped with valve systems as in diffusive photoacoustic sensors. However, the active noise cancellation systems, devices and methods of the present invention can be used to improve photoacoustic sensors sensitivity in photoacoustic sensors including valve systems.

As illustrated, for example, in connection with FIG. 8, the measurement volumes of the present invention preferably are formed to have a curved surface substantially or totally throughout the inner surface area thereof. In the illustrated embodiments, measurement volumes 60 and 160 are spherical in shape (other than in the plane of operative connection with the generally planar surface of a window 162 separating infrared light source 165 from measurement volume 160). See, for example, FIG. 8. In many currently available photoacoustic sensors, the measurement volume is cylindrical in shape or otherwise includes sharply angle corners or intersections, resulting in non-uniform distribution of light throughout. Further, a generally spherical volume provides for more efficient heating of the gas in the measurement volume should the photoacoustic sensor contain the analyte gas.

In several embodiments of the present invention, as, for example, illustrated in FIGS. 2-8, the bodies of the photoacoustic sensors were machined from a solid block of aluminum.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A photoacoustic sensor for measuring an analyte gas in an environment, the photoacoustic sensor comprising a sensor system for photoacoustic detection, at least one noise canceling pressure sensor a control system in operative connection with the noise canceling pressure sensor to actively cancel the effects of noise in the environment on the sensor system, and a speaker, the speaker being operative to be driven with a signal generally inverse to an output signal of the noise cancelling pressure sensor.

2. The photoacoustic sensor of claim 1 wherein the sensor system includes a measurement volume, a source of light energy and a photoacoustic pressure sensor.

3. The photoacoustic sensor of claim 2 wherein the noise canceling pressure sensor is a first microphone and the photoacoustic pressure sensor is a second microphone.

4. The photoacoustic sensor of claim 2 wherein the noise canceling pressure sensor is in acoustic connection with an initial volume, which is in connection with the measurement volume, the photoacoustic sensor further comprising a barrier between the measurement volume and the initial volume.

5. The photoacoustic sensor of claim 4 wherein the barrier between the measurement volume and the initial volume is a first diffusion element operative to attenuate pressure waves while allowing diffusion of analyte gas molecules therethrough.

6. The photoacoustic sensor of claim 5 further comprising a second diffusion element positioned between the initial volume and an inlet of the photoacoustic gas sensor, the second diffusion element being operative to attenuate pressure waves while allowing diffusion of analyte gas molecules therethrough.

7. The photoacoustic sensor of claim 6 wherein the first diffusion element and the second diffusion element are sintered metal elements.

8. The photoacoustic sensor of claim 4 further comprising a source of light energy, the measurement volume having an inner surface that is continuously curved over substantially the entire inner surface other than where a window in optical connection with the source of light intersects the measurement volume.

9. The photoacoustic sensor of claim 4 wherein the volume of the initial volume is no greater than ten times the measurement volume.

10. The photoacoustic sensor of claim 4 wherein the volume of the initial volume is no greater than five times the measurement volume.

11. The photoacoustic sensor of claim 4 wherein the volume of the initial volume is no greater than the measurement volume.

12. The photoacoustic sensor of claim 4 further comprising at least one vibration canceling sensor that is not in acoustic connection with the measurement volume or with the environment.

13. The photoacoustic sensor of claim 12 wherein the photoacoustic pressure sensor is a first microphone and the vibration canceling sensor is a second microphone.

14. A photoacoustic sensor for measuring an analyte gas in an environment, the photoacoustic sensor comprising a measurement volume, a source of light energy, a photoacoustic microphone, and at least one vibration canceling sensor, wherein the vibration canceling sensor is not in acoustical connection with the measurement volume or with the environment.

15. The photoacoustic sensor of claim 14 wherein the vibration canceling sensor is a microphone.

16. The photoacoustic sensor of claim 14 further comprising at least one noise canceling pressure sensor and a control system in operative connection with the noise canceling pressure sensor to actively cancel the effects of noise in the environment on the sensor system.

17. The photoacoustic sensor of claim 16 wherein the noise canceling pressure sensor is a microphone.

18. The photoacoustic sensor of claim 16 further comprising a speaker, the speaker being operative to be driven with a signal generally inverse to an output signal of the noise canceling sensor.

19. The photoacoustic sensor of claim 14 wherein the measurement volume has an inner surface that is continuously curved over substantially the entire inner surface other than where a window in optical connection with the source of light intersects the measurement volume.

20. The photoacoustic sensor of claim 19 wherein the inner surface is spherical over substantially the entire inner surface other than where the window intersects the measurement volume.

* * * * *